(12) United States Patent
Ravenscroft et al.

(10) Patent No.: US 6,458,145 B1
(45) Date of Patent: Oct. 1, 2002

(54) INTRA VASCULAR SNARE AND METHOD OF FORMING THE SAME

(75) Inventors: Adrian C. Ravenscroft, Rochester, MA (US); Paul R. Gianneschi, Snellville, GA (US)

(73) Assignee: Hatch Medical L.L.C., Sneville, GA (US)

( * ) Notice: Subject to any disclaimer, the term of this patent is extended or adjusted under 35 U.S.C. 154(b) by 8 days.

(21) Appl. No.: 09/722,826

(22) Filed: Nov. 28, 2000

(51) Int. Cl.[7] .................................................. A61F 2/01
(52) U.S. Cl. ...................... 606/200; 606/127; 606/205; 606/206
(58) Field of Search ............................ 606/1, 200, 113, 606/159, 127, 205, 206; 623/1.19; 600/151; 604/95.05

(56) References Cited

U.S. PATENT DOCUMENTS

| | | | |
|---|---|---|---|
| 3,828,790 A | 8/1974 | Curtiss et al. | |
| 4,665,906 A | 5/1987 | Jervis | |
| 5,098,440 A | 3/1992 | Hillstead | |
| 5,133,733 A | * 7/1992 | Rasmussen et al. | |
| 5,171,233 A | 12/1992 | Amplatz et al. | |
| 5,709,704 A | * 1/1998 | Nott et al. | |
| 5,817,104 A | 10/1998 | Bilitz et al. | |
| 6,077,274 A | 6/2000 | Ouchi et al. | |
| 6,099,534 A | 8/2000 | Bates et al. | |
| 6,214,025 B1 | * 4/2001 | Thistle et al. | |
| 6,280,451 B1 | * 8/2001 | Bates et al. | .................. 606/127 |
| 6,290,721 B1 | * 9/2001 | Heath | |

* cited by examiner

Primary Examiner—Michael H. Thaler
(74) Attorney, Agent, or Firm—Nixon Peabody LLP; Donald R. Studebaker

(57) ABSTRACT

The intravascular snare is formed with a central shaft which is attached to the proximal ends of a plurality of loops. The loops are connected together at joinder points spaced from both the distal and proximal ends of the loops to maintain the relative geometry of the loops in both an expanded and compressed condition. The loops include a material which provides radiopacity.

29 Claims, 3 Drawing Sheets

INTRA VASCULAR SNARE AND METHOD OF FORMING THE SAME

BACKGROUND OF THE INVENTION

In recent years, a number of medical devices have been designed which are adapted for compression into a small size to facilitate introduction into a vascular passageway and which are subsequently expandable into contact with the walls of the passageway. Such devices have often been formed of shape memory material, such as nitinol, an alloy of titanium and nickel. Shape memory in such devices can be thermally triggered or stress induced.

In the thermally triggered devices, the device is cooled below a temperature transformation level to a martensitic state and thereby softened for loading into a catheter in a relatively compressed and elongated state. To regain the memorized shape in an austenitic state, the device is warmed to a selected temperature transformation level, such as human body temperature. The two interchangeable shapes are possible because of the two distinct microcrystalline structures that are interchangeable with a small variation in temperature. The temperature at which the device assumes its first configuration may be varied within wide limits by changing the composition of the alloy. Thus, for human use, the alloy may be focused on a transition temperature range close to 98.6° F.

For stress induced shape memory as described by U.S. Pat. No. 4,665,906 to Jervis, stress is applied to a shape memory device which is in the austenitic state at room temperature. As the alloy forming the device is deformed elastically, it enters the martensitic state and can be loaded into a catheter or delivery tube. When the stress is removed, the alloy recovers elastically and reverts to austenite without requiring a change in temperature. The recovery always returns the material to the initial shape present in the austenitic phase before stress was applied.

The development of intra vascular medical devices such as stents and filters which expand and are held in position by engagement with the inner wall of a vessel has led to the development of intra vascular snares to retrieve these foreign bodies from the peripheral vessels of the cardiovascular system. Single loop snares, such as those shown by U.S. Pat. No. 3,828,790 to Curtiss et al. and U.S. Pat. No. 5,171,233 to Amplatz et al. are commonly used snares. The Amplatz snare consists of a super-elastic nitinol cable with a single-formed loop. Because of the snare's super elastic construction, the loop can be introduced through small lumen catheters without risk of deformation. The loop is formed at approximately 90° to the cable, and this allows for the user to advance the loop over a foreign body and ensnare it by closing the loop with a small catheter. The foreign body is removed from the vasculature by withdrawing the device into a guiding catheter or vascular sheath. Although this snare is a significant improvement over earlier forward facing stainless steel snares that are easily deformed and difficult to advance over foreign bodies, the Amplatz snare is geometrically sensitive and requires appropriate sizing to the vasculature in order to allow for successful ensnarement. In addition, the single loop design has poor cross sectional vessel coverage and thereby requires skilled manipulation to capture the desired object.

In an attempt to provide a snare with improved cross sectional vessel coverage, multi loop snares such as those shown by U.S. Pat. No. 5,098,440 to Hillstead and U.S. Pat. No. 6,099,534 to Bates have been developed. These snares include loops which are joined only at their proximal ends to a shaft, and otherwise are not joined at any point between the shaft and the distal ends of the loops. This provides the advantage over single loop. snares of enhanced cross sectional vessel coverage, and the free distal ends of the loops can be brought together to engage multiple surfaces of an intravascular medical device to be removed. The problem with multiloop snares having loops attached at only the proximal ends is that the relative geometry of the free loops is difficult to maintain. The relative position of the loops can change, both within a catheter or delivery tube and within a vessel, and the loops can actually become displaced or entangled during delivery.

Basket type snares having loops connected at both their proximal and distal ends to form an enclosed basket have been developed as shown by U.S. Pat. No. 5,817,104 to Bilitz et al. and U.S. Pat. No. 6,077,274 to Ouchi et al. These basket snares do not have free distal ends which can move along opposed surfaces of an intravascular device, and basket snares are primarily used to remove stones or stone fragments from the gallbladder, bilary tract, renal pelvis and ureter.

SUMMARY OF THE INVENTION

It is a primary object of the present invention to provide a novel and improved intravascular snare and method of forming the same wherein the snare includes multiple loops which are free at their distal ends and are joined at their proximal ends and at positions between the proximal and distal ends.

Another object of the present invention is to provide a novel and improved intravascular snare and method of forming the same wherein the snare includes a plurality of loops which are interlaced together between their proximal and distal ends to maintain a predetermined loop geometry while maintaining the distal ends of the loops free.

A further object of the present invention is to provide a novel and improved intravascular snare and method of forming the same wherein the snare includes a plurality of loops attached at their proximal ends to a central shaft. The loops angle outwardly relative to the shaft at approximately a ten to thirty degree angle and spaced from the shaft are angled outwardly at about another ten to thirty degrees to create a greater diameter at the loop distal ends. The total angle of each loop to the shaft is preferably forty degrees or less.

Yet another object of the present invention is to provide a novel and improved intravascular snare and method of forming the same wherein the snare includes multiple loops of a composite multiple strand material with the strands of each loop being penetrated by an adjacent loop to interlace the loops together.

A still further object of the present invention is to provide a novel and improved intravascular snare and method of making the same wherein the snare is formed of shape memory material such as nitinol. Martensite is induced in the material, such as by cooling, and in the martensitic state, the material is deformed mechanically to form a new shape by controlled deformation. If cycled elastically, the alloy will remember the new shape rather than the original austenitic shape.

These and other objects of the present invention are achieved by forming a snare comprised of a central shaft constructed of super-elastic nitinol with two to eight preformed interlaced loops at the distal end of the shaft. The loops are formed of equal length and preferably extend at approximately 15° to the central shaft and each loop is also preferably flared outwardly an additional 15° to open the leading edges of the loops to a greater diameter that ultimately increases wire to vessel surface area contact. Individual loops are interlaced together to form a tulip shaped assembly. The loops are fonxed from a composite multiple strand material constructed of nitinol and a noble metal such as gold or platinum iridium. The noble metal provides radiopacity while the nitinol provides shape memory.

DESCRIPTION OF THE PREFERRED EMBODIMENTS

Figure 1:
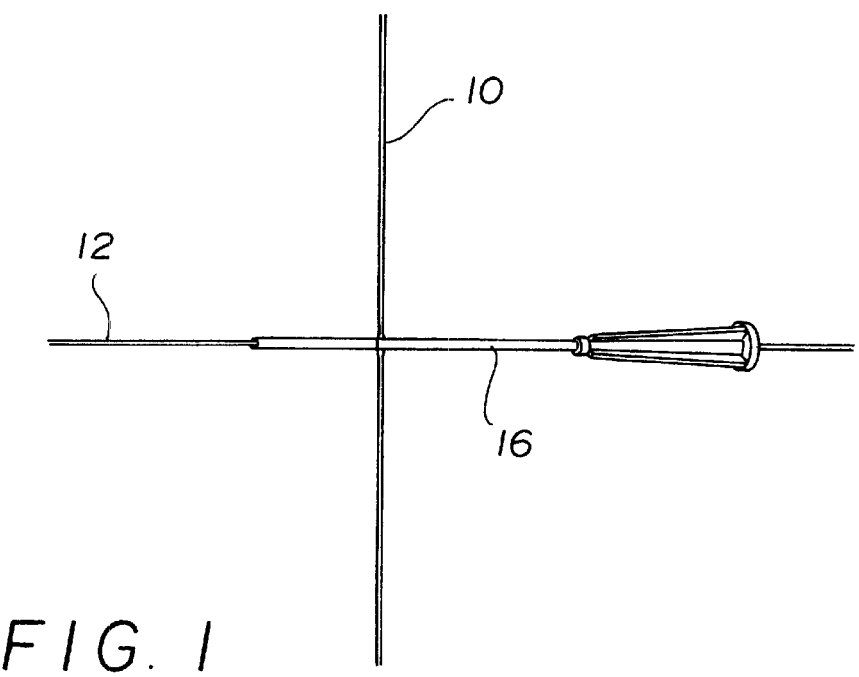
FIG. 1 is a plan view of the interlacing of two strands used to form the loops for the intravascular snare of the present invention.
Figure 2:
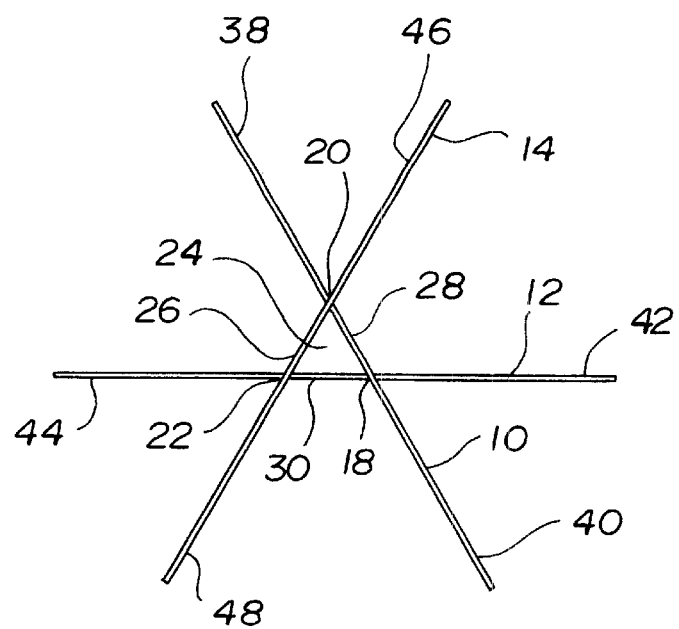
FIG. 2 is a plan view of three interlaced strands used for the intravascular snare of the present invention.

Referring to FIGS. 1 and 2, the loops of the intravascular snare of the present invention are formed from three wires 10, 12, and 14 each of which is formed preferably of a multistrand composite. This composite is preferably constructed of nitinol and a noble metal such as gold or platinum iridium, so that the noble metal provides radiopacity while the nitinol provides shape memory. The multiple strands forming the wires 10, 12 and 14 can be braided, knitted, woven or wound. Other materials could be used to form the loops such as beta-titanium, MP35N, stainless steel, and possibly fibers such as Dacron (polyester) or Kevlar. To interlace the multiple strand wires 10, 12 and 14, a fine gauge hypothermic needle 16 is used to penetrate between the strands of the wire 10 so that approximately fifty percent of the strands forming the wire are on each side of the needle. Then the wire 12 is passed through the hypodermic needle and the wire 10 as shown in FIG. 1, and the hypodermic needle is withdrawn. This creates an interlaced joinder point 18 between the wires 10 and 12.

The hypodermic needle is passed through the wire 14 at two spaced locations as shown in FIG. 2. In a first location 20, the wire 10 is passed through the hypodermic needle and the wire 14 to form an interlaced joinder point and at a second location 22, the wire 12 is passed through the hypodermic needle and the wire 14 to form an interlaced joinder point. Once the three wires are interlaced, they form an isosceles triangle 24, the size of which dictates the ultimate diameter of the intravascular snare. The portions of the wires 10, 12, and 14 which form the three sides 26, 28 and 30 of the triangle 24 are then moved outwardly to form the distal closed ends of loops 32, 34 and 36 shown in FIG. 3. These distal loop ends, which extend outwardly beyond the joinder points 18, 20 and 22 are also numbered 26, 28 and 30 in FIG. 3.

It should be recognized that although three loops formed from three wires 10, 12, and 14 are preferred for the intravascular snare of the present invention, the snare could be formed from two interconnected wires or from more than three wires. For example, if the snare is formed from four wires with four loops, the interlaced joinder points will form a square rather than the isosceles-triangle 24; in a five wire snare the joinder points will form a pentagon; in a six wire snare the joinder points will form a hexagon; etc. In each case, the equal sided geometric interconnection formed by the joinder points dictates the ultimate diameter of the intravascular snare.

To complete the formation of the loops 32, 34 and 36, the free ends 38 and 40 of the wire 10, 42 and 44 of the wire 12 and 46 and 48 of the wire 14, which extend outwardly beyond the joinder points 18, 20 and 22, are gathered sequentially to a central point for attachment to a shaft 50. The loops 32, 34 and 36 are of equal size, and are interlaced at joinder points 18, 20 and 22 which are spaced inwardly from loop distal ends 26, 28 and 30, leaving the loop distal ends free to close against the sides of an object to be removed from a vessel.

Once the loops 32, 34 and 36 are formed, the snare 52 is positioned on a forming jig to form the geometry of the loops. They extend from the shaft 50 at angles of approximately fifteen degrees, and spaced from the end of the shaft, each loop flares outwardly for approximately another fifteen degrees to open the distal ends of the loops to a greater diameter that ultimately increases wire to vessel surface area contact. The loops can be formed to other combined angles which will provide loops which extend up to forty degrees with respect to the shaft 50.

In practice, the side view geometry of each loop can be described as a radius and the front view geometry described as a teardrop. Individual loops are interlaced together to form a tulip assembly, and the relative position and geometry of the loops is maintained by the joinder points 18, 20, 22. These prevent the loops from becoming displaced or crossed in a catheter or delivery tube. It should be noted that when the loops are interlaced in the manner shown in FIGS. 1 and 2, the wire side of a loop which passes between the strands of an adjacent loop is adapted for limited longitudinal movement relative to the adjacent loop at the joinder point. This relieves stress on the interconnection at the joinder point as the loops expand and contract.

After the loop geometry is formed, the snare 52 is annealed at approximately 500° C. for ten minutes. To further enhance radiopacity, the loops can be coated with noble metals by dip casting or ion disposition. A preferred method is by an unbalanced magnetron sputtering process providing a well-adhered noble coating on the outside surfaces of the braid. This will prevent coating fracture during loop deformation.

Radiopacity can also be achieved without a coating process by fabricating one or more strands of the multistrand material forming the loop from a radiopaque material such as a noble metal or from a tubular strand filled with a radiopaque material. In some instances, the wires 10, 12 and 14 may be formed from a single strand of wire filled with a radiopaque material.

The snare 52 may be formed of nitinol wire or similar thermally responsive shape memory material, and may then be cooled to the martensitic state for insertion into a catheter or delivery tube. When the snare is projected outwardly from the delivery tube within a blood vessel, it can be formed to return to the austenitic state in response to body temperature and expand outwardly into contact with the vessel walls.

The snare 52 offers significant design advantages over known single loop and multiple loop retrieval systems. The snare 52 extends across the entire cross sectional area of a vessel while in contrast, a single loop snare, if oversized or undersized relative to the vessel cross section, leaves large, uncovered voids within the vessel. The snare 52 is self sizing to vasculature over a larger range requiring minimal device manipulation in use, and forms to a variety of vessel diameters and geometries. Unlike other single and multiple loop snares, the snare 52 conforms with a consistent geometry to a vessel due to the interlacing of the loops.

Figure 4:
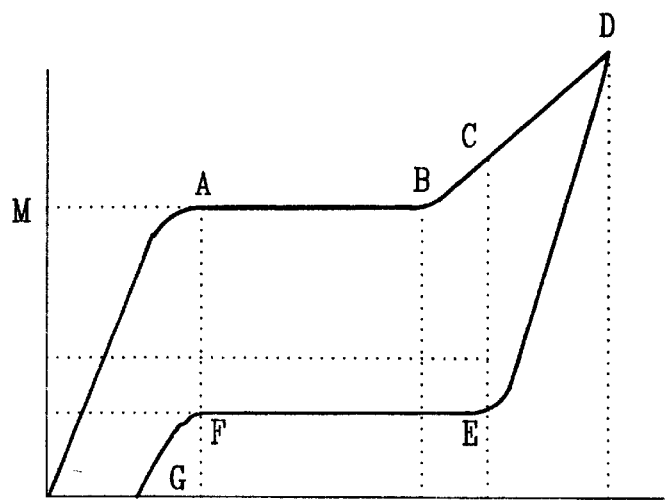
FIG. 4 is a diagram of the martensitic deformation used to size the intravascular snare of the present invention.

Referring now to FIG. 4, the shape memory of a nitinol medical device, such as the snare 52, can be altered by mechanical deformation in the martensitic state. Martensite can be thermally induced in the alloy by cooling, and once martensitic, the alloy is permanently deformed mechanically along line CD in FIG. 4. As the alloy is subsequently warmed, it recovers along line E F G to a permanent set that is approximately equal to the permanent deformation of the martensite.

To obtain the same result with stress induced martensite, stress is applied to the alloy, it deforms elastically along line OA, by SIM along line AB, by elastic deformation of the martensite to point C, and then eventually by permanent deformation of the imartensite along line CD. As the stress is removed, the alloy partially recovers from D to E (does not recover permanent deformation); then, at a critical stress, the alloy reverts to austenite without requiring a change in temperature. This reversion occurs at constant stress that is lower than that of an elastically deformed alloy (no martensite deformation). Finally, if the stress is removed from the reverted austenite, it recovers elastically along line FG to a permanent set that is approximately equal to the permanent deformation of the martensite.

By shaping a device in accordance with one of the above methods, the material can have one shape remembered in the austenitic phase if elastically cycled and a second shape can be formed by controlled deformation in the martensite phase. Once the new shape is formed, the material will remember the new shape if cycled elastically. Thus a medical device in the martensitic state can be crushed within a delivery device to alter the remembered austenitic shape of the medical device.

It is the intention of the invention to provide a multi-looped intra-vascular snare that provides improved wall coverage and larger indicated range (vessel diameters). As with all snares, its ability to ensnare a variety of foreign objects and visibility under fluoroscopy are both very important design attributes. It is believed that these design requirements have been met by providing multiple loops for ensnarement and radiopaque fillers, Although we have specified three loop snares, it is plausible to have a two to eight looped system for specific retrieval purposes.

Although we have selected multistrand shape memory wire as our preferred loop material, it could be substituted with tubing with radiopaque fillers, drawn wire, plastics, and other general engineered materials commonly used in the medical device industry. Loops of the snare could be welded, bonded, knotted, and/or crimped together to substitute for strand interlacing. Also, the wires forming the loops can be tapered lengthwise from the shaft 50 to provide a lower profile device and to optimize the radial strength of the snare.

Figure 3:
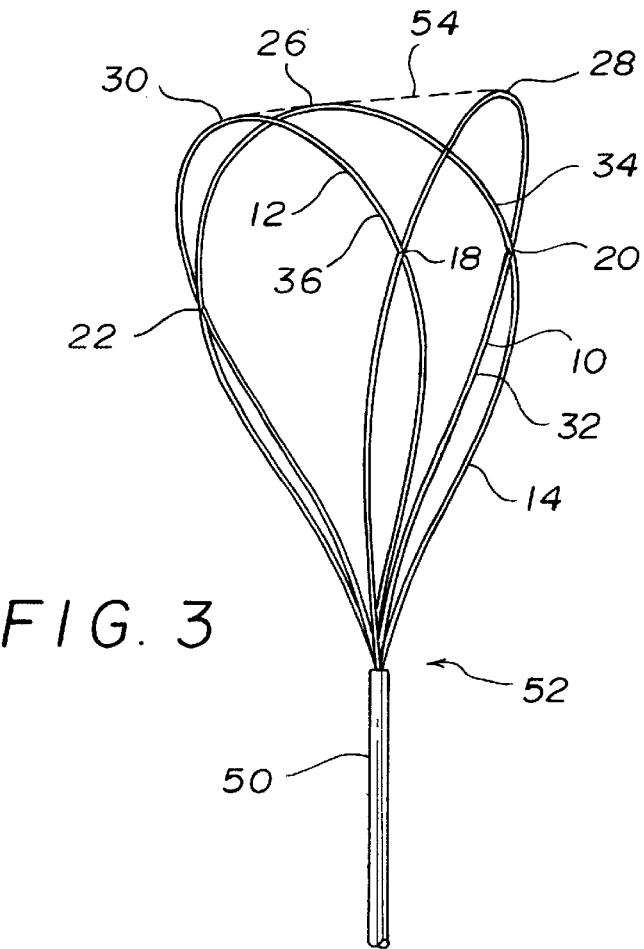
FIG. 3 is a view in side elevation of the intravascular snare of the present invention.
Figure 5:
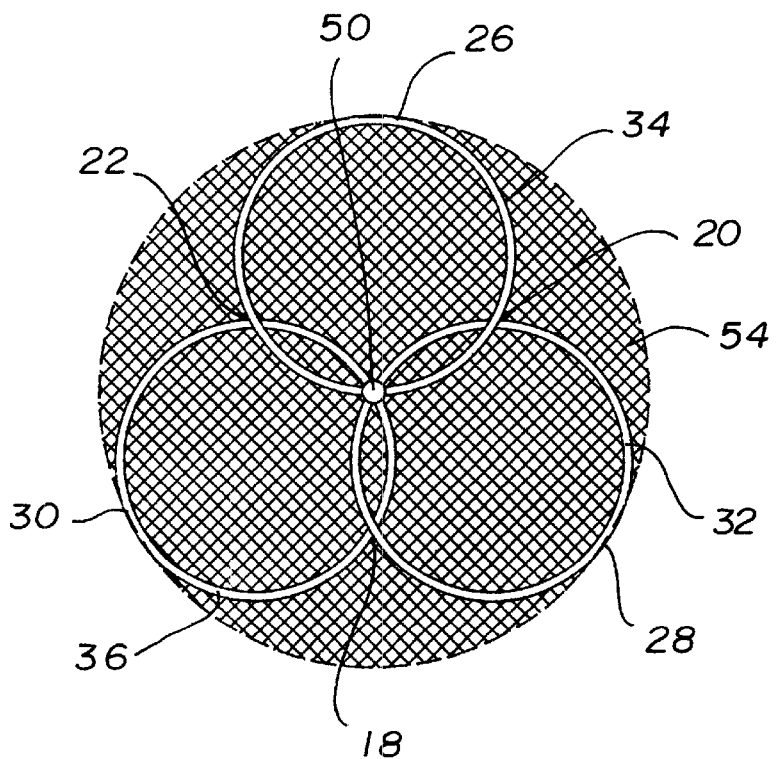
FIG. 5 is a view in end elevation of the expanded intravascular snare of FIG. 3.

As shown in broken lines in FIG. 3 and in FIG. 5, a thin, flexible membrane or sheet of materials 54 may be attached to points on the distal ends of each of the loops 32, 34 and 36 to stretch across the distal ends of the loops when the loops are in the expanded, open position. This membrane would in turn stretch across a vessel containing the snare 52 to capture clots or foreign objects.

Figure 6:
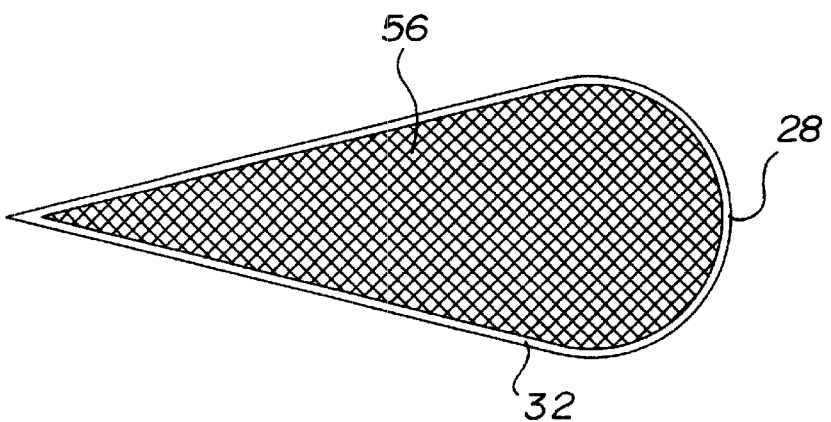
FIG. 6 is a view in side elevation of a loop for the intravascular snare of FIG. 3 covered by a membrane.

Also, as shown in FIG. 6, each of the loops 32, 34 and 36 can be covered, either totally or partially, with a thin, flexible membrane, weave or fabric 56 to assist in capturing clots or tissue.

We claim:

1. An intravascular snare comprising:
 a plurality of adjacent elongate loops each having a proximal end and a looped distal end, the distal end of each of said loops being free and not interconnected with adjacent loops,
 said loops are formed of shape memory material having an austenitic and martensitic state being curved at the distal end of the loop to form two elongate, spaced sides for the loop which angle toward one another from the distal end to the proximal end of the loop,
 each side of each said loop being directly interconnected with a side of an adjacent loop at only one joinder point spaced from the proximal and distal end thereof, and
 a shaft connected to the proximal ends of said loops, said proximal ends being gathered together at said shaft.

2. The intravascular snare of claim 1 wherein the joinder points between the sides of said loops form an equal sided geometric figure.

3. The intravascular snare of claim 2 wherein each of said loops is formed of multistrand material.

4. The intravascular snare of claim 3 wherein said multistrand material includes a material which provides radiopacity.

5. The intravascular snare of claim 3 wherein each of said joinder points is formed by interlacing a side of one loop through the strands of the side of an adjacent loop.

6. The intravascular snare of claim 1 wherein the joinder points for all of said plurality of loops are equally spaced relative to the proximal and distal ends of said loops.

7. The intravascular snare of claim 6 wherein each loop adjacent to the proximal end thereof extends laterally outward from said shaft at a first angle and at a point spaced between the shaft and the distal end of said loop angles laterally outward at a second angle.

8. The intravascular snare of claim 1 wherein said loops are interconnected to permit limited movement between adjacent loops at said joinder point.

9. The intravascular snare of claim 8 wherein a thin flexible sheet of material is attached to the distal end of each of said loops to extend across said loops between the distal ends thereof.

10. The intravascular snare of claim 8 wherein a thin flexible sheet of material is secured to each of said loops to extend across said loop.

11. The intravascular snare of claim 1, further comprising a thin flexible sheet of material attached to the distal end of each of said loops to extend across said loops between the distal ends thereof.

12. An intravascular snare comprising:
 at least three adjacent loops which are equal in length each having a proximal end and a looped distal end, the distal end of each of said loops being free and not interconnected with adjacent loops,
 said loops are formed of shape memory material having an austenitic and martensitic state with each said loop including a plurality of strands being interconnected with an adjacent loop at a joinder point spaced from the proximal and distal end thereof, the joinder points between said loops forming an equal sided geometric figure by separating strands of one loop forming a space and passing the adjacent loop directly through the space formed between the strands of the one loop, and a shaft connected to the proximal ends of said loops, said proximal ends being gathered together at said shaft.

13. The intravascular snare of claim 12, further comprising a thin flexible sheet of material attached to the distal end of each of said loops to extend across said loops between the distal ends thereof.

14. An intravascular snare comprising:

a plurality of adjacent loops each formed of multistrand material and each having a proximal end and a looped distal end, the distal end of each of said loops being free and not interconnected with adjacent loops, each said loop being interconnected with an adjacent loop at a joinder point spaced from the proximal and distal end thereof, each of said joinder points being formed by separating strands of one loop forming a space and passing the adjacent loop directly through the space formed between the strands of the one loop, and a shaft connected to the proximal ends of said loops, said proximal ends being gathered together at said shaft.

15. The intravascular snare of claim 14 wherein the multistrand material of each said loops includes a material which provides radiopacity.

16. The intravascular snare of claim 15 wherein said material which provides radiopacity is a noble metal.

17. The intravascular snare of claim 16 wherein said multistrand material includes a shape memory material having an austenitic and a martensitic state.

18. The intravascular snare of claim 17 which includes at least three loops.

19. The intravascular snare of claim 18 wherein the joinder points between said loops form an isosceles triangle.

20. The intravascular snare of claim 14, further comprising a thin flexible sheet of material attached to the distal end of each of said loops to extend across said loops between the distal ends thereof.

21. An intravascular snare comprising:

at least three adjacent loops each formed of multistrand braided material and each having a proximal end and a looped distal end, the distal end of each of said loops being free and not interconnected with adjacent loops, each said loop being interconnected with an adjacent loop at a joinder point spaced from the proximal and distal end thereof, each of said joinder points being formed by separating strands of one loop forming a space and passing the adjacent loop directly through the space formed between the strands of the one loop wherein the joinder points between the loops form an isosceles triangle, a shaft connected to the proximal ends of said loops, said proximal ends being gathered together at said shaft, and each loop adjacent to the proximal end thereof extends laterally outward from said shaft at substantially a fifteen degree angle and at a point spaced between said shaft and the distal end of said loop angles laterally outward for substantially an additional fifteen degrees.

22. The intravascular snare of claim 21 wherein said multistrand braided material is a shape memory material having an austenitic and a martensitic state.

23. The intravascular snare of claim 21, further comprising a thin flexible sheet of material attached to the distal end of each of said loops to extend across said loops between the distal ends thereof.

24. A method for altering the remembered shape of a medical device formed of shape memory material having an austenitic and a martensitic state which includes forming the medical device to have a first remembered shape in the austenitic state, causing the medical device to enter the martensitic state, mechanically deforming the medical device while in the martensitic state, and causing the medical device to return to the austenitic state and a new second remembered shape resulting from the mechanical deformation in the martensitic state which is different from said first remembered shape.

25. The method of claim 24 wherein stress is applied to the medical device to cause stress induced martensite, such stress being maintained while mechanically deforming the medical device, and subsequently removing the stress from the medical device to return the medical device to the austenitic state and the new second remembered shape.

26. An intravascular snare comprising:

at least three elongate loops of substantially equal length each having a proximal end and a looped distal end, the distal end of each of said loops being See and not interconnected with adjacent loops, each loop being formed of a length of elongate material curved at the distal end of the loop to form two elongate spaced sides for the loop, each of which terminates at a free end of the proximal end of the loop, each side of each said loop being directly interconnected at only one joinder point with a side of an adjacent loop and each loop is directly interconnected at two joinder points to two adjacent loops, the joinder points for all of said plurality of loops being spaced from the proximal and distal ends of said loops and substantially equally spaced relative to said proximal and distal ends wherein the joinder points between the loops form an isosceles triangle, and a shaft connected to the proximal ends of said loops, the free ends of the sides of said loops being gathered together at said shaft, each said loop adjacent to the proximal end thereof extending laterally outward at an angle from said shaft.

27. The intravascular snare of claim 26, wherein each loop is formed from a separate piece of multistrand wire, each of said joinder points being formed by. passing the piece of multistrand wire forming one loop directly through the strands of multistrand wire forming adjacent loops.

28. The intravascular snare of claim 27, wherein each loop adjacent to the proximal end thereof extends laterally outward from the shaft at a first angle and at a point spaced between the shaft and the distal end of said loop angles laterally outward at a second angel relative to the shaft.

29. The intravascular snare of claim 27, further comprising a thin flexible sheet of material attached to the distal end of each of said loops to extend across said loops between the distal ends thereof.

* * * * *